United States Patent [19]

Boussignac

[11] Patent Number: 5,616,890
[45] Date of Patent: Apr. 1, 1997

[54] BINAURAL STETHOSCOPE ALLOWING SURROUNDING NOISES TO BE HEARD

[76] Inventor: Georges Boussignac, 1, Avenue de Provence, 92160 Antony, France

[21] Appl. No.: 552,102

[22] Filed: Nov. 2, 1995

[30] Foreign Application Priority Data

Aug. 29, 1995 [FR] France ................... 95 10156

[51] Int. Cl.⁶ ........................ A61B 7/02
[52] U.S. Cl. ..................... 181/131; 181/137
[58] Field of Search .................... 181/131, 137; 381/67

[56] References Cited

U.S. PATENT DOCUMENTS

| | | | |
|---|---|---|---|
| 2,271,467 | 1/1942 | Smithline | 181/131 |
| 3,314,499 | 4/1967 | Blackman | 181/131 |
| 3,515,239 | 6/1970 | Machlup et al. | 181/131 |
| 4,239,089 | 12/1980 | Nelson | 181/131 |

*Primary Examiner*—Khanh Dang
*Attorney, Agent, or Firm*—Fisher, Christen & Sabol

[57] ABSTRACT

A stethoscope comprising two earpieces (1,2) which are connected to an endpiece (3) for capturing sounds via a route for transmission (4 to 7) of the captured sounds, the endpiece being held in one hand by a practitioner during auscultation of a patient. According to the invention, the transmission route (4 to 7) comprises a closable orifice (9) which, in the open position, is capable of bringing the transmission route into sound communication with the surroundings, and whose closing and opening are controlled by the hand holding the endpiece.

5 Claims, 2 Drawing Sheets

BINAURAL STETHOSCOPE ALLOWING SURROUNDING NOISES TO BE HEARD

BACKGROUND OF THE INVENTION

1. Field of the Invention

The present invention relates to a binaural stethoscope allowing surrounding noises to be heard.

2. Background Art

It is known that binaural stethoscopes have two earpieces which are each intended to bear against the entrance to the auditory channels of a practitioner and which are connected to an endpiece for capturing sounds, said endpiece being placed by said practitioner on certain areas of the body of a patient. For this purpose, the practitioner holds the endpiece in one of his hands and places it against the body of the patient during auscultation. The two earpieces are connected to the endpiece for capturing sounds via a route for transmission of the captured sounds, which route generally comprises two rigid tubular branches which at one end support the earpieces and which at the other end are joined to said endpiece via a flexible T-tube system forming part of said transmission route.

When the practitioner has put said earpieces into his ears and has placed the endpiece against the body of the patient, he does not hear, or at least does not hear distinctly, the surrounding noises, but only the sounds emanating from the body of the patient and being transmitted to him via the stethoscope.

Under these conditions, when the patient speaks to the practitioner during auscultation, said practitioner cannot catch what is being said to him. Now, experience has shown that during this type of auscultation patients express themselves more openly to their practitioner and provide him with information which is useful in establishing a diagnosis. Of course, the practitioner is then forced to remove at least one of the earpieces from his ear and to ask the patient to repeat what has just been said. The spell is then broken, and the patient does not repeat the same confidences exactly or even remains silent.

Furthermore, during auscultation, external noises from the surroundings may interfere with the sounds being listened to by the practitioner through the stethoscope, and the practitioner may well want to know the exact nature of the sound interference.

SUMMARY OF THE INVENTION

Against this background, the present invention relates to an improved stethoscope allowing surrounding noises to be heard without the practitioner having to alter the position of his hand holding the patient, nor that of his other hand holding the endpiece against said patient.

To this end, according to the invention, the stethoscope comprising two earpieces which are connected to an endpiece for capturing sounds via a route for transmission of the captured sounds, said endpiece being held in one hand by a practitioner during auscultation of a patient, is distinguished by the fact that said transmission route comprises a closable orifice which, in the open position, is capable of bringing said transmission route into sound communication with the surroundings, and whose closing and opening are controlled by said hand holding said endpiece.

Thus, when the practitioner needs to listen to surrounding noises or sounds during auscultation, he can do so without substantially altering his posture and his position in relation to the patient, simply by moving one of the fingers of his hand holding the endpiece. During the auscultation itself, that is to say while listening to the sounds emanating from the patient, the practitioner uses his hand holding said endpiece in order to close said orifice of the transmission route, whereas when the practitioner wishes to hear external sounds or noises, it suffices for him to open said orifice by moving said hand. At this point, the transmission route is open to the outside in such a way that the surrounding sounds and noises reach the ears of the practitioner by way of that part of the transmission route which is arranged between said orifice and said earpieces.

In a first embodiment, in which said transmission route comprises, in a conventional manner, a flexible tube connected to said endpiece, said closable orifice consists of a hole formed in the wall of said flexible tube in proximity to the endpiece.

As an alternative, said closable orifice can be provided directly on the endpiece.

For example, when the endpiece comprises, again in a conventional manner, two opposite bells which are capable of being brought alternately into communication with a common chamber opening into said transmission route, said closable orifice can be provided at the level of said common chamber, between said bells.

For the purpose of making it easier to control the opening or closing of said orifice, the latter can be continued outward from said transmission route via a rigid projecting tube integral therewith. In order to permit better capture of the sounds, and also better closing of the parallel route for listening to surrounding noise, the extremity of said rigid tube opposite said orifice can be flared in a trumpet shape.

When manual closure is envisaged, the flared extremity of said rigid tube has a diameter which is such that it can be closed with the aid of the pulp of a single finger of said hand.

As an alternative, the extremity of the rigid tube opposite said orifice can of course be closed with the aid of a movable closing piece which can be controlled by the practitioner's hand which is holding the endpiece.

In one particular embodiment in which the endpiece comprises the two opposite bells mentioned hereinabove, it is advantageous if said rigid projecting tube is on the opposite side of said common chamber from said transmission route.

BRIEF DESCRIPTION OF THE DRAWINGS

The figures in the attached drawing will show clearly how the invention can be realized. In these figures, identical reference numbers designate similar elements.

DETAILED DESCRIPTION OF THE INVENTION

Figure 1:
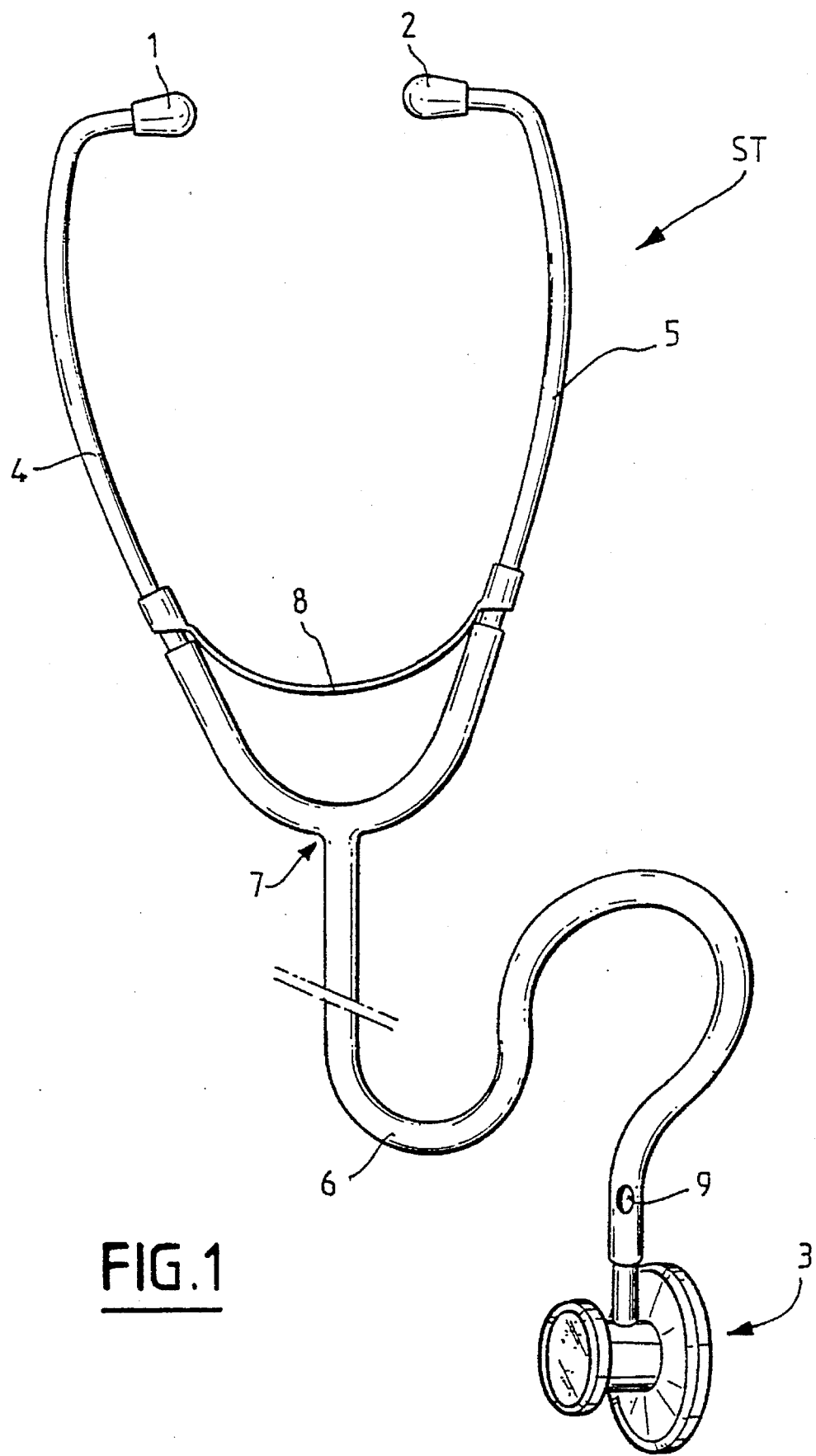
FIG. 1 shows an improved stethoscope in accordance with a first embodiment of the present invention.

The stethoscope ST shown schematically in FIG. 1 comprises, in a known manner, two earpieces 1 and 2 which are connected to an endpiece 3 for capturing sounds via a route for transmission of the captured sounds comprising two rigid tubular branches 4 and 5 which are connected to a flexible tube 6 via a T-shaped branch 7.

A resilient strip 8 holds the rigid branches 4 and 5, bringing them together, and the endpiece 3 is fitted in the extremity of the tube 6 opposite the T-shaped junction piece 7. Thus, when the stethoscope ST is used in the normal way, the practitioner draws the rigid branches 4 and 5 of the stethoscope apart, counter to the action of the strip 8, and places the earpieces 1 and 2 respectively in his ears, in which they are held by the elastic action of the strip 8. With one of his hands, generally the left hand, the practitioner holds the patient, and with his other hand, generally the right hand, he places the endpiece 3 on an area of the body of said patient.

In order to remedy the abovementioned disadvantages of the known stethoscopes, the stethoscope according to the present invention and represented in FIG. 1 additionally comprises an orifice 9 formed in the tube 6 in proximity to the endpiece 3. When the practitioner wishes to listen only to the sounds emanating from the body of the patient, he closes said orifice 9, for example by means of the pulp, of the index finger of his hand holding the endpiece 3 placed against the patient.

On the other hand, when the practitioner wishes to listen to noises or sounds external to the patient, he frees the orifice 9 in such a way that these external noises and sounds reach him through the tube 6, the junction piece 7, the branches 4 and 5 and the earpieces 1 and 2, without his having to change his posture in relation to the patient or remove one or other, or both, of the two branches of the stethoscope from his ears.

Figure 2:
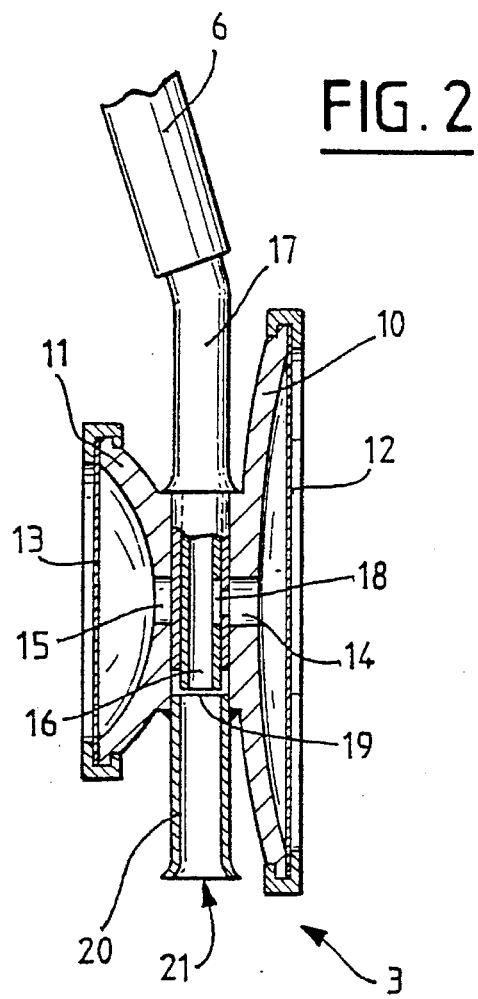
FIG. 2 shows an axial cross section of the endpiece of an improved stethoscope in accordance with a second embodiment of the present invention.
Figure 3:
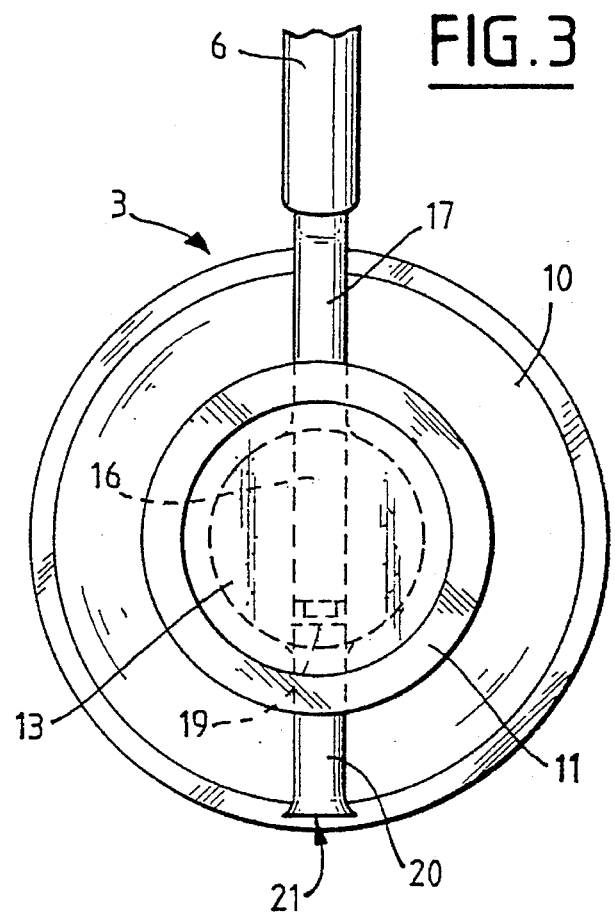
FIG. 3 is a front view of the endpiece in FIG. 2.

In the embodiment represented in FIGS. 2 and 3, the endpiece comprises, in a conventional manner, two bells 10 and 11, of different sizes, which are in each case associated with a vibrating membrane 12 or 13 intended to be placed on the skin of the patient. Said bells can communicate alternately, via openings 14 or 15, with a common chamber 16 which is connected to the flexible tube 6 via a rigid bent joining piece 17. This joining piece 17 can turn inside the endpiece 3 in such a way as to bring an orifice 18 into line with one or other of the conduits 14 or 15 and thereby connect one or other of said bells 10 and 11 to the earpieces 1 and 2.

The endpiece 3 as it has been described hereinabove is known.

According to the present invention, a known endpiece of this type is improved by means of an orifice 19 being drilled in the wall of the common chamber 16, diametrically opposite the bent tube 17. Moreover, the orifice 19 is continued outward from said endpiece via a rigid tube 20 which is integral therewith, which is arranged between said bells and which is flared at its extremity 21 opposite the orifice 19.

It will be readily understood that during auscultation the practitioner can open or close the flared extremity 21 of the tube 20 with the aid of one of his fingers (for example the index finger of his hand holding the endpiece against the patient) in such a way as to permit or to prevent the transmission of the external noises and sounds to his ears.

Figure 4:
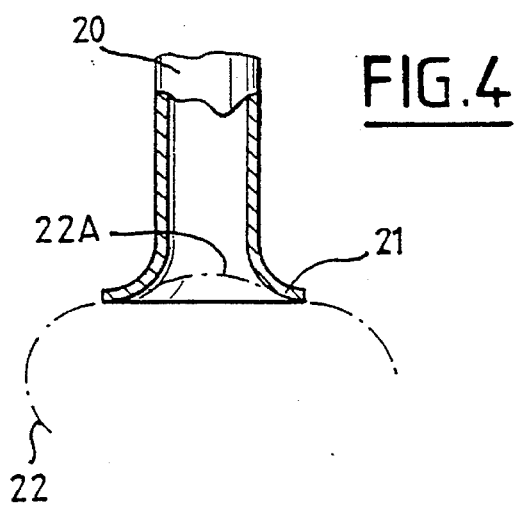
FIG. 4 illustrates the manual closure of the flared tube provided, in accordance with the invention, on the endpiece in FIGS. 2 and 3.

It will also be noted, as illustrated by FIG. 4, that when the practitioner presses the pulp of one of his fingers to a greater or lesser extent against the flared opening 21 of the tube 20, he will cause a greater or lesser amount of said pulp to penetrate inside said tube, thereby slightly modifying the length of the transmission route and thus the quality of the transmission of the sounds emanating from the patient. It can be seen that if the pulp 22 of a finger is lightly applied against the flared opening 21, this pulp lies flush with said opening. By contrast, if the pulp 22 is pressed strongly against the flared opening 21, a portion of said pulp designated by 22A in FIG. 4 penetrates inside the rigid tube 20.

It will also be noted that if the rotary joining piece 17 is brought into a position in which said orifice 18 is not in line either with the conduit 14 or the conduit 15, the practitioner completely eliminates the transmission of the sounds emanating from the body of the patient and is able to listen exclusively to the voice of said patient and to the external sounds.

Figure 5:
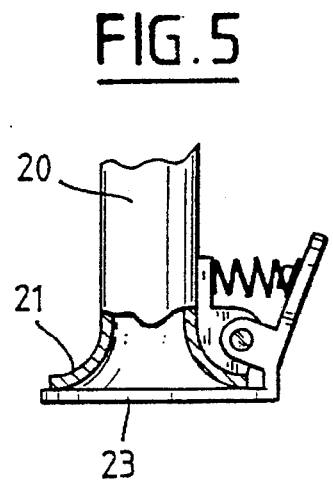
FIG. 5 illustrates, as an alternative, a closing piece provided for controlling the passage of sounds through the rigid tube of the endpiece in FIGS. 2 and 3.

As an alternative to the manual closure provided for in FIGS. 2 to 4, a closing piece 23 can be provided, for example of the type with a spring provided on certain wind instruments, in order to close the flared extremity 21 (see FIG. 5).

I claim:

1. A stethoscope comprising:

two earpieces (1,2);

a sound connection (4 to 7) connecting said earpieces (1,2) to;

an endpiece (3), said endpiece (3) being held in one hand by a practitioner during auscultation of a patient and having a common chamber (16) disposed between two opposite bells (10, 11) which are capable of being brought alternately into communication with said common chamber (16) of said endpiece (3), wherein said endpiece (3) has an orifice (19) in sound communication with said common chamber (16) and connected to a rigid projecting tube (20) integral to and extending outward from said endpiece (3), said rigid projecting tube (20) having an end orifice (21) opposite said common chamber (16) and in sound communication with the surroundings, wherein closing and opening of said end orifice (21) are controlled by said hand holding said endpiece (3).

2. The stethoscope as claimed in claim 1, wherein said end orifice (21) is flared in a trumpet shape.

3. The stethoscope as claimed in claim 2, wherein said flared end orifice (21) of said rigid projecting tube (20) has a diameter which is such that it is covered by a pulp (22) of a single finger of said hand.

4. The stethoscope as claimed in claim 2, wherein said rigid projecting tube (20) further comprises a movable closing piece (23) covering and pivotally attached to said flared end orifice (21).

5. The stethoscope as claimed in claim 2, wherein said rigid projecting tube (20) is on the opposite side of said common chamber (16) from said sound connection (17, 4 to 7).

* * * * *